United States Patent

Schneider et al.

[11] Patent Number: 5,645,604
[45] Date of Patent: Jul. 8, 1997

[54] TIBIA PLATFORM FOR A KNEE JOINT PROSTHESIS

[75] Inventors: Markus Schneider, Amriswil; Walter Moser, Herrenschwanden, both of Switzerland

[73] Assignees: Sulzer Medizinaltechnik AG, Winterthur; Protek AG, Muensing/Bern, both of Switzerland

[21] Appl. No.: 625,441

[22] Filed: Mar. 27, 1996

[30] Foreign Application Priority Data

Apr. 20, 1995 [EP] European Pat. Off. .............. 95810263

[51] Int. Cl.$^6$ ...................................................... A61F 2/38
[52] U.S. Cl. .................................... 623/20; 623/18
[58] Field of Search ............................ 623/16, 18, 20

[56] References Cited

U.S. PATENT DOCUMENTS 4,944,757  7/1990  Martinez .
5,330,534  7/1994  Herrington .

FOREIGN PATENT DOCUMENTS 0 495 340  7/1992  European Pat. Off. .

*Primary Examiner*—David Isabella
*Attorney, Agent, or Firm*—Townsend and Townsend and Crew LLP

[57] ABSTRACT

With the invention there is shown a C-shaped clip as a compression member (8) which can be inserted into a pocket (15) of a joint support (4) and which can itself be secured in this pocket against falling out of place by a latched arrangement. In this arrangement the two limbs of the clip act transversely to their spring direction as a spacer between a spring tongue (5) and a shoulder which are formed on the joint support (4). In this way a simple securing device arises which is recessed in the joint support (4) and which prevents springing back of the latched spring tongue (5) and is only loaded in compression. In the installed state the spring tongue (5) is not itself subjected to any alternating bending loads.

3 Claims, 1 Drawing Sheet

TIBIA PLATFORM FOR A KNEE JOINT PROSTHESIS

BACKGROUND OF THE INVENTION

The invention is concerned with a tibia platform for a knee joint prosthesis comprising an anchoring part for the attachment to a tibia bone and a joint support which can be latched via at least one spring tongue formed on it to the anchoring part by resilient deflection and snapping into place.

An embodiment of this kind is shown in the patent application EP-A-0 495 340 in which a joint support is prevented from dropping out of place by a spring tongue. A system of this kind does not however preclude forces occurring between the anchoring part and the joint support in the latched state which act in the spring-back direction of the spring tongue and which bring about a repeated springing back of the spring tongue.

SUMMARY OF THE INVENTION

The object of the invention is to provide assistance with respect to this circumstance. This object is satisfied in accordance with the characterizing part of independent patent claim 1 in that a shoulder is formed on the joint support in the spring-back direction of the spring tongue in order to provide an intermediate space with a defined spacing from the spring tongue; and in that a compression member can be inserted into the intermediate space when the joint support is latched and fills out the latter in order to prevent springing back of the spring tongue.

An advantage of this arrangement is the fact that the compression member and the spring tongue are only loaded in the inserted state in compression and not in bending when forces occur in the spring-back direction. A further advantage is that the position of the spring tongue can be checked with the inserted compression member since the compression member can only be inserted with a fully latched spring tongue. Since the forces can only arise at the compression member in one direction, namely in the spring-back direction of the spring tongue, the compression member can itself be secured in the joint support by a latched arrangement which is not influenced by alternating pressure forces. Since the compression member is essentially only loaded by alternating compression forces, not only metals but also plastics are possible materials for this member.

DESCRIPTION OF THE PREFERRED EMBODIMENTS

Figure 1:
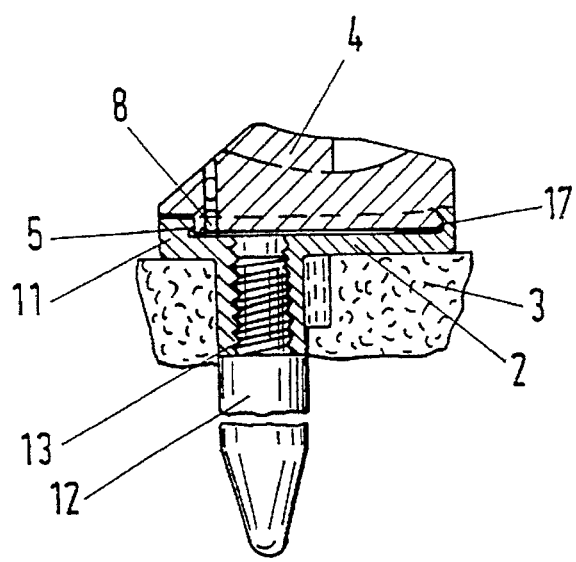
FIG. 1 illustrates a latched engagement of a joint support with an anchoring part made in accordance with the present invention.

In the drawings a C-shaped clip is shown as the compression member 8 which can be inserted into a pocket 15 of a joint support 4, and which can itself be secured in this pocket 15 against falling out of place via a latched arrangement. The two limbs of the clip act transversely to their spring direction as a spacer between a spring tongue or pawl 5 and a shoulder which are formed on the joint support 4. In this way a simple security device arises which is recessed in the joint support 4, which prevents springing back of the latched in spring tongue 5 and which is only loaded in compression. In the installed state the spring tongue 5 is itself not subjected to any alternating bending loads.

Figure 4:
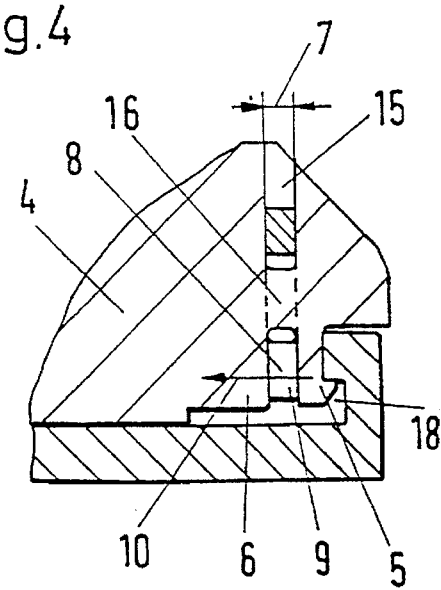
FIG. 4 is an enlarged longitudinal section through the joint support illustrated in FIG. 2 in the region of the spring tongue made in accordance with the present invention.
Figure 5:
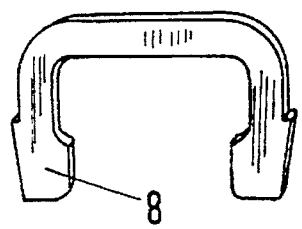
FIG. 5 is an enlarged view of a compression member in the form of a clip.
Figure 2:
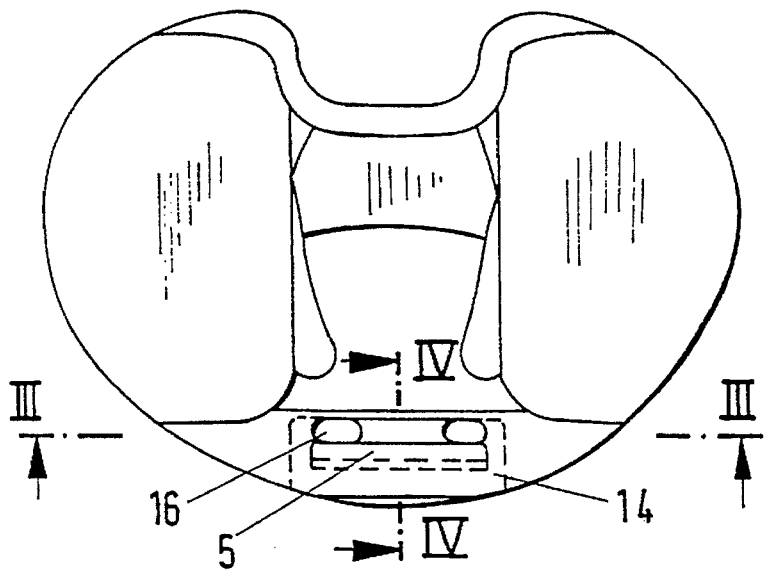
FIG. 2 is a plan view of a joint support which is latchable with a compression member made in accordance with the present invention.
Figure 3:
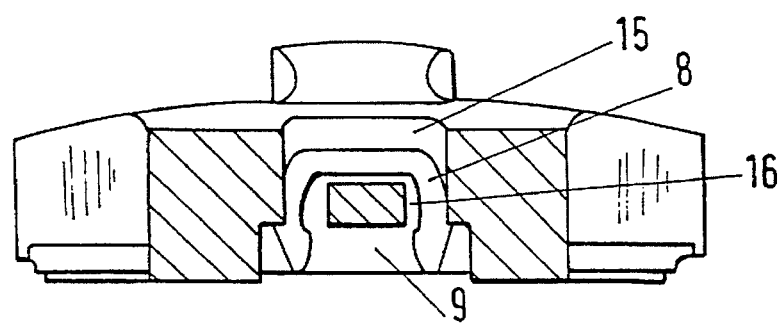
FIG. 3 is a partial cross-section view taken along the intermediate space in FIG. 2 for the compression member made in accordance with the present invention.

A tibia platform 1 (FIG. 1) comprises an anchoring part 2 of metal into which an anchoring spigot 12 is screwed via a thread 13 in order to anchor the latter in the tibia bone 3 for an artificial knee joint. The anchoring part has an upwardly projecting edge 11 which has regions with grooves at the inner side. In the posterior region these grooves form an open hinge 17 with the joint support 4, whereas in the anterior region (FIG. 4) a spring tongue 5 which is worked into the joint support 4 latches into the groove 18 in order to hold the joint support in the anchoring part. During the latching into place, the spring tongue 5 is thrust backwardly in the spring-back direction 10 and could also be subjected to alternating bending loads in the latched state when unfavorable forces are acting. For this reason a pocket 15 is formed in the spring-back direction 10 behind the spring tongue 5 and opens via two connection openings 16 into an intermediate space 9 which is defined by a precise distance 7 between the spring tongue 5 and a shoulder 6 lying opposite to it in the spring back direction. A compression member 8 in the form of a clip corresponds in thickness to the spacing 7 and can be inserted from above into the pocket 15 until it is, on the one hand, latched transversely to the spring-back direction 10 and, on the other hand, fills out the intermediate space 9 in order to prevent return springing of the spring tongue and thus loading of the spring tongue 5 in bending. The clip can be inserted from above outside of the actual joint guidance surface and sunk in position. Since it is in practice only loaded in compression it can be executed in various materials. In the metallic embodiment its position can be checked on an X-ray screen.

We claim:

1. A tibia platform (1) for a knee joint prosthesis comprising an anchoring part (2) for the attachment to a tibia bone (3) and a joint support (4), the joint support (4) being configured for latching to the anchoring part (2) by resilient deflection and snapping into place of at least one spring tongue (5) formed on said joint support (4); wherein a shoulder (6) is formed on the joint support (4) in a spring-back direction (10) of the spring tongue (5) in order to provide an intermediate space (9), said shoulder (6) having a defined spacing (7) from the spring tongue (5); and wherein a compression member (8) configured to be inserted into the intermediate space (9) when the joint support (4) is latched, said compression member (8) filling out the intermediate space (9) in order to prevent springing back of the spring tongue (5).

2. A tibia platform (1) in accordance with claim 1, wherein the compression member (8) is configured to be secured on the joint support (4).

3. A tibia platform (1) in accordance with claim 2, wherein the compression member (8) is a C-shaped clip having leg members, each leg member having means formed thereon to latch to cooperating structures in the joint support (4) to thereby secure the compression member (8) on the joint support (4).

* * * * *